United States Patent [19]

Kurita

[11] Patent Number: 5,105,627
[45] Date of Patent: Apr. 21, 1992

[54] CRYOPRESERVATION CONTAINER OF ANIMAL CELL

[75] Inventor: Susumu Kurita, Tokyo, Japan

[73] Assignee: Nihon Freezer Co., Ltd., Tokyo, Japan

[21] Appl. No.: 512,201

[22] Filed: Apr. 20, 1990

[51] Int. Cl.⁵ .......................... F25D 3/08; F25D 3/10; C12N 5/00; A01N 1/02
[52] U.S. Cl. .......................................... 62/62; 62/337; 62/371; 62/457.1; 62/457.2
[58] Field of Search ............... 62/62, 337, 371, 457.1, 62/457.2, 457.9

[56] References Cited

U.S. PATENT DOCUMENTS

| | | | |
|---|---|---|---|
| 4,404,820 | 9/1983 | Romaine | 62/457.2 X |
| 4,470,264 | 9/1984 | Morris | 62/457.2 X |
| 4,498,312 | 2/1985 | Schlosser | 62/457.2 |
| 4,688,398 | 8/1987 | Baek | 62/457.2 X |
| 4,958,506 | 9/1990 | Guilhem et al. | 62/371 X |
| 4,974,423 | 12/1990 | Pring | 62/371 |
| 4,981,234 | 1/1991 | Slaughter | 62/457.1 X |

FOREIGN PATENT DOCUMENTS

| | | | |
|---|---|---|---|
| 0601335 | 7/1960 | Canada | 62/457.2 |
| 3142521 | 7/1983 | Fed. Rep. of Germany | 62/62 |
| 2168054 | 7/1987 | Japan | 62/62 |
| 1-04163 | 4/1989 | Japan | 62/62 |
| 658901 | 12/1986 | Switzerland | 62/62 |
| 1143949 | 3/1985 | U.S.S.R. | 62/62 |
| 1332120 | 8/1987 | U.S.S.R. | 62/62 |
| 2186067 | 8/1987 | United Kingdom | 62/457.2 |
| 8301994 | 6/1983 | World Int. Prop. O. | 62/457.1 |

*Primary Examiner*—Henry A. Bennett
*Assistant Examiner*—Christopher Kilner
*Attorney, Agent, or Firm*—Sandler, Greenblum & Bernstein

[57] ABSTRACT

A cryopreservation container comprising a bottomed cylindrical hollow container body, a lid which is removably attached to the container body to close the hollow portion thereof, and heat conductivity-retarded liquid enclosed in the hollow portion of the container body.

19 Claims, 2 Drawing Sheets

CRYOPRESERVATION CONTAINER OF ANIMAL CELL

BACKGROUND OF THE INVENTION

1. Field of the Invention

The present invention relates to a cryopreservation container for freezing and preserving an animal cell.

2. Description of Related Art

Recently, animal cells have been used to produce various substances or to develop various medicines. To this end, it is necessary to preserve the animal cell to be used. The cellular life span is extremely short, and accordingly, the cell must be maintained by subcultivating the cell in a culture medium.

However, the culture condition depends on the kind of cell, and accordingly culturing is troublesome and takes a long time. Furthermore, a cross-substitution or a cross-penetration tends to occur between the cells, or the cell may be contaminated with a microorganism. Furthermore, a cell, having a characteristic to be easily degenerated must be preserved before degeneration starts. In particular, a gene-recombination type of animal cell aimed at a production of substances or hybridoma which bears an antibody or the like changes in property during culture, resulting in waste of valuable resources. The change in property must be checked when the cell is used.

It is known to use an ampoule or a tube in which the animal cell is enclosed together with a freezing culture medium to be frozen and preserved. As a freezing means can be used a deep freezer of about $-80°$ C. which is widely used in works or laboratories. Recently, liquid nitrogen has been used as a freezing means, since a good result can be obtained when an animal cell is preserved at as low temperature as possible below $-100°$ C. In this method of using liquid nitrogen, since it is not necessary to culture the cell, no degeneration of the cell occurs.

The animal cell must be frozen slowly rather than quickly, since quick freezing causes the cell to be extinguished or deactivated. If the ampoule or tube is directly put in the deep freezer or liquid nitrogen atmosphere, the animal cell enclosed in the ampoule or tube is quickly cooled, thus resulting in an extinction or deactivation of cell. As a matter of course, the extinct or deactivated animal cell is useless, so that the cryopreservation is meaningless.

The primary object of the present invention is to provide a cryopreservation container in which an animal cell can be slowly frozen in an existing deep freezer.

SUMMARY OF THE INVENTION

The inventors of the present invention have conceived a utilization of specific liquid having a low or least heat conductivity (heat conductivity-retarded liquid) to slowly freeze an animal cell.

To achieve the above-mentioned object, according to the present invention, there is provided a cryopreservation container comprising a bottomed cylindrical hollow container body, a lid which is removably attached to the container body to close the same, and heat conductivity-retarded liquid enclosed (filled) in the container body.

The "heat conductivity-retarded liquid" referred to herein means liquid having a low or least heat conductivity.

The heat conductivity-retarded liquid renders it possible to provide a slow cooling rate (freezing speed) needed for the slow freezing of an animal cell. Preferably, the heat conductivity-retarded liquid is selected so that when the ambient temperature (outside air temperature) of the cryopreservation container is $-60°$ C. $\sim -100°$ C., the cooling rate in the cryopreservation container is about $-0.5°$ C./min $\sim -2°$ C./min.

For example, the heat conductivity-retarded liquid can be a solution of acetone and water, ethanol, etc. It has been experimentally confirmed that good results are obtainable when the heat conductivity liquid comprises $20 \sim 40$ volume % of acetone in water.

The lid can be made of a heat insulative solid material. However, preferably, the lid is made of a hollow body in which heat conductivity-retarded liquid is enclosed.

The container body is preferably made of high heat insulative synthetic resin, such as polyethylene.

An enclosure container in which an animal cell to be frozen and preserved is enclosed together with cryopreservation medium can be stored in the cryopreservation container. Contrary to the cryopreservation container, the enclosure container is preferably made of a heat conductive metal tube, such as aluminum or aluminum alloy.

BRIEF DESCRIPTION OF THE DRAWINGS

The invention will be described below in detail with reference to the accompanying drawings, in which.

DESCRIPTION OF PREFERRED EMBODIMENTS

Figure 1:
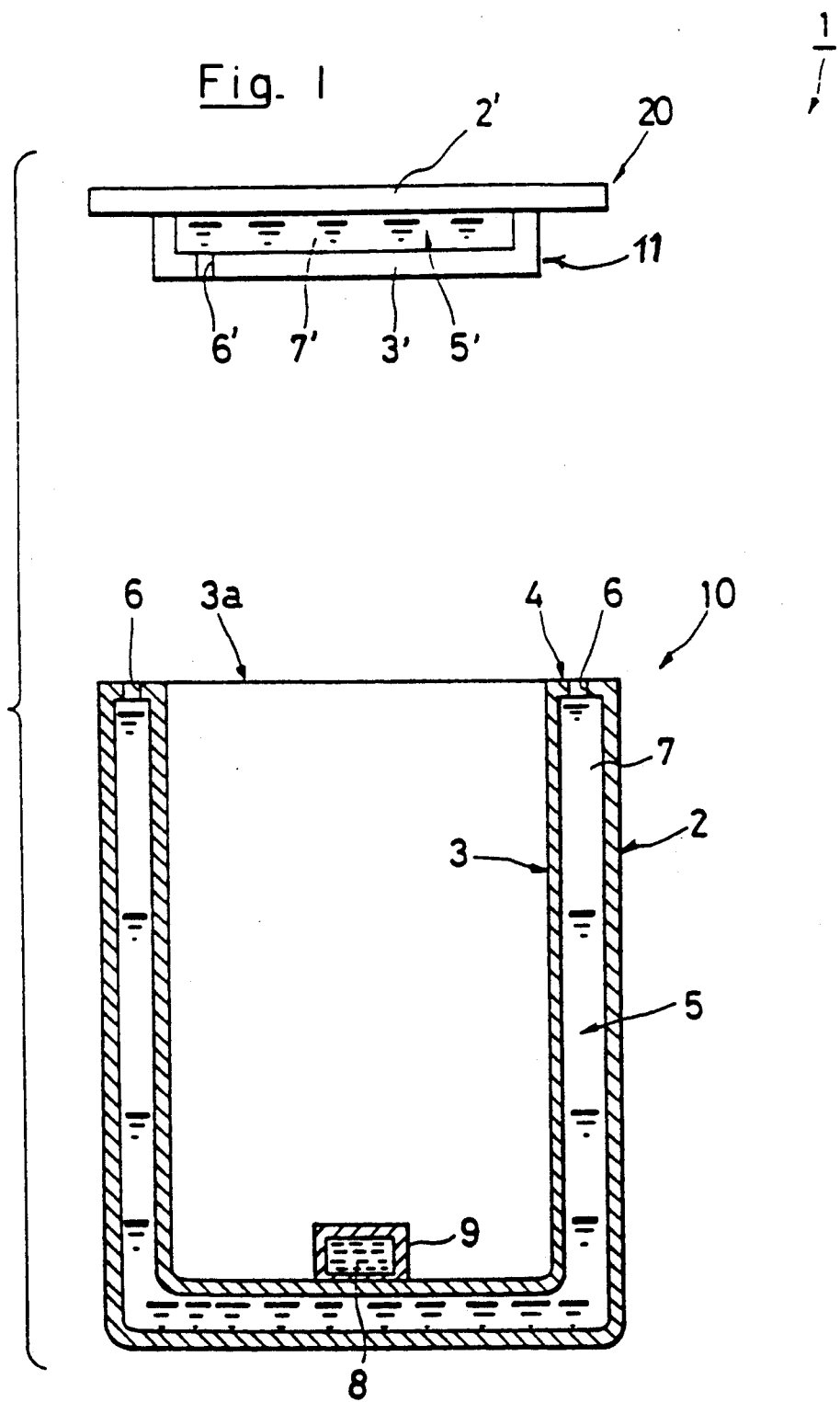
FIG. 1 is a partial sectional view of a cryopreservation container according to an embodiment of the present invention; and, FIG. 2 is a diagram showing an experimental result of a freezing speed in a cryopreservation container shown in FIG. 1.

FIG. 1 shows a cryopreservation container according to an embodiment of the present invention. The cryopreservation container 1 essentially has a container body 10 and a lid 20. The container body 10 has a bottomed, outer cylinder 2 and a bottomed, inner cylinder 3 which is spaced from the outer cylinder 2. The inner and outer cylinders 2 and 3 are made of a heat insulative synthetic resin, such as polyethylene.

The height and the diameter of the outer cylinder 2 are larger than those of the inner cylinder 3. The upper ends of the outer and inner cylinders 2 and 3 are connected to each other by a ring member 4, so that a bottomed cylindrical hollow portion 5 is defined by and between the inner and outer cylinders 3 and 2 and the ring member 4. The ring member 4 has one or more inlet ports 6 through which heat conductivity-retarded liquid 7 is introduced in the hollow portion 5 to be enclosed therein. The inlet ports 6 are closed by appropriate means, for example, by welding, e.g., ultrasonic welding, after the heat conductivity-retarded liquid 7 is enclosed in the hollow portion 5.

The lid 20 is detachably attached to the container body 10 to close an upper opening 3a of the container body 10. In a manner similar to the container body 10, the lid 20 has an outer circular plate 2', an inner circular plate 3' having a generally U-shaped cross section, and a hollow portion 5' which is defined between and by the inner and outer plates 3' and 2'. Heat conductivity-retarded liquid 7', identical to the heat conductivity-retarded liquid 7, is enclosed in the hollow portion 5'. The inner plate 3' has an inlet port 6' through which the heat conductivity-retarded liquid 7' is introduced in the hollow portion 5'. The inlet port 6' is closed by an appropriate means, for example, by welding, e.g., ultrasonic welding, after the heat conductivity-retarded liquid 7' is enclosed in the hollow portion 5'.

In an alternative, it is possible to make the lid 20 of a heat insulative solid body, such as a styrofoam. In this alternative, no heat conductivity-retarded liquid 7' is enclosed in the lid 20.

The heat conductivity-retarded liquid 7 (or 7') is selected, taking the volume of the hollow portion 5 into account, so that when the ambient temperature of the cryopreservation container 1 is $-60°$ C. $\sim -100°$ C., the cooling rate (freezing speed) in the cryopreservation container 1 is $-0.5°$ C./min $\sim -2°$ C./min, and preferably about $-1°$ C./min. Acetone in water, or ethanol can be used as the heat conductivity-retarded liquid. Preferably, 20~40 volume % of acetone in water, and most preferably 30 volume % of acetone in water, containing distilled water can be particularly advantageously used.

An enclosure container 9 in which an animal cell (not shown) to be frozen and preserved is enclosed together with a freezing cryopreservation medium 8 is received in the inner cylinder 3 of the cryopreservation container 1. The enclosure container 9 is made of a hollow prismlike tube of metal, such as aluminum or aluminum alloy. As the cryopreservation medium 8 can be used 10 volume % of dimethyl sulfoxide, 15 volume % of Calf Fetal Bovine Serum, and 75 volume % of Eagle's M.E.M. Earle's-base (Note: these components are prepared with carbon dioxide and sodium bicarbonate to exhibit PH 6.8~PH 7.0). The cell density to the cryopreservation medium 8 is preferably about $1 \times 10^7 \sim 5 \times 10^6$/ml.

Although the enclosure container 9 is made of an aluminum or aluminum alloy hollow prism in the illustrated embodiment, the invention is not limited thereto. Namely, for example, the enclosure container 9 can be made of a hollow cylindrical metal body or an ampoule of glass, metal or slug.

When the cryopreservation container is used to freeze an animal cell, the cell to be frozen and preserved is suspended in the cryopreservation medium 8 to be enclosed in the enclosure container 9. Thereafter, the opening of the enclosure container 9 is closed. After that, the enclosure container 9 is put on the bottom of the inner cylinder 3, and thereafter, the mount 11 formed by the inner plate 3' of the lid 20 is fitted in the inner cylinder 3 to close the opening 3a of the cryopreservation container 1.

Thereafter, the cryopreservation container 1 is put in a deep freezer (not shown) of about $-80°$ C. Consequently, the animal cell in the enclosure container 9 in the cryopreservation container 1 is slowly and gradually cooled and frozen at a low cooling speed. When the temperature of the animal cell is descended to $-80°$ C, the animal cell is stably maintained at $-80°$ C.

If the animal cell should be preserved at a lower temperature, for instance 2~4 hours after, the cryopreservation container 1 is transferred to a liquid nitrogen atmosphere in which the animal cell is cooled to a temperature below $-80°$ C.

When thawing the frozen animal cell to reculture the same, the enclosure container 9 is taken out from the cryopreservation container 1 housed in the deep freezer and is then forcedly shaken in hot water to thaw the cryopreservation medium 8. Immediately thereafter, the enclosure container 9 is put in iced water to be cooled.

After that, the animal cell is taken out from the enclosure container 9 and is then cleaned by a centrifugal separator, so that growth medium which is not cooled is added to the animal cell to prepare an appropriate number of cell in order to culture the same.

Figure 2:
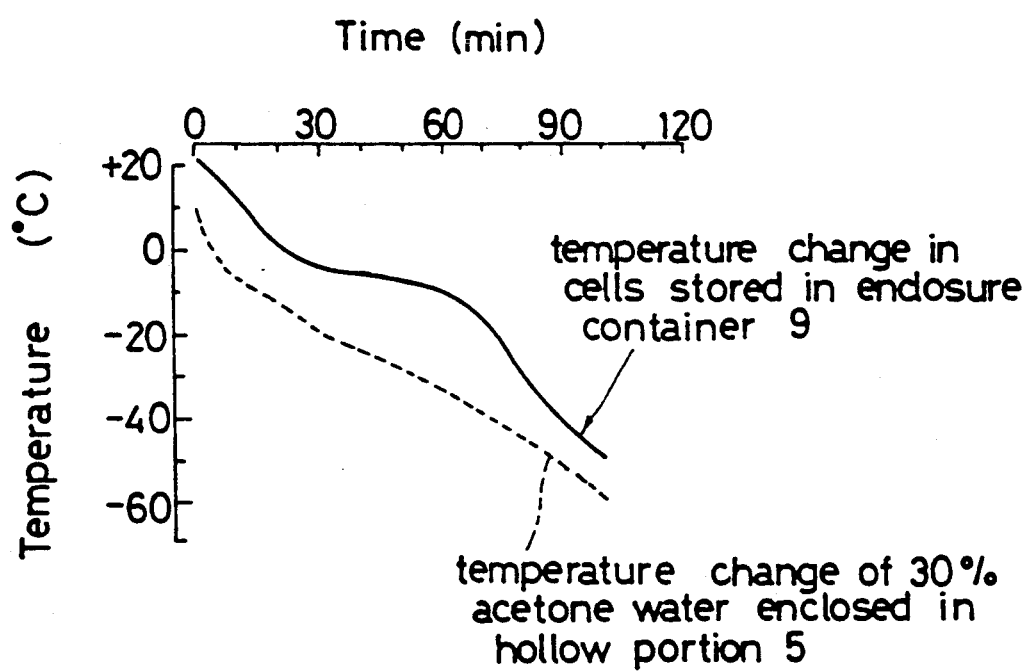

It was experimentally confirmed that a preferable cooling speed (freezing speed) is about $-1°$ C./min. According to the present invention, a cooling speed very close to the desired cooling speed (about $-1°$ C./min) was obtained, as can be seen in FIG. 2. The experimental result shown in FIG. 2 was obtained under the following conditions.

| | |
|---|---|
| Height of outer cylinder 2 | 72 mm |
| Diameter of outer cylinder 2 | 62 mm |
| Height of inner cylinder 3 | 62 mm |
| Diameter of inner cylinder 3 | 47 mm |
| Material of outer and inner cylinders 2 and 3 polyethylene | |
| Volume of hollow portion 5 | 100 ml |
| Quantity of acetone water | 100 ml |
| Temperature of deep freezer | $-80°$ C. (constant) |

Composition of Cryopreservation Medium (F.S. Medium)
- 10 volume % of dimethyl sulfoxide
- 15 volume % of Calf Fetal Bovine Serum
- 75 volume % of Eagle's M.E.M. Earle's-base
- PH 6.8~PH 7.0 (adjusted by addition of carbon dioxide and sodium bicarbonate)

The viability and transplantability of the animal cells which were preserved by the cryopreservation container 1 of the present invention under the above-mentioned conditions are shown in Table 1-Table 3 below. It is noted that freezing times are indicated in years except where indicated, and the symbol + denotes that the solid tumors were transplantable. Furthermore, in Table 3, the Biocell Number (%) denotes the survival rate of live cells after thawing, with the Viable Cell Count depicting the ratio, thawing/freezing.

TABLE 1

| Name of Cell | Freezing Time (Year) | Viable Cell Count |
|---|---|---|
| HeLa - S$_3$ | 8 | 95.5 |
| Vero | 10 | 90 |
| BHK21-Cl$_{13}$ | 12 | 65 |
| Human Cell | 12 | 75 |
| MDCK | 7 | 85 |
| L$_{929}$ | 10 | 85 |
| FM$_3$A | 12 | 93 |
| Avian Embryo | 13 | 55 |

TABLE 2

| Solid Tumor Name of Tumor | Name of Host-Animal | Freezing Time (year) & Transplantability |
|---|---|---|
| W-256 | Rat, Wister-Imamichi | 2+ |
| X5563 | Mouse C3H/He | 2.5+ |
| NF-Sarcoma | Mouse ddy | 3+ |
| Fructo Sarcoma | Mouse ddy | 3+ |
| Ms-147 | Mouse C57BL | 2+ |
| SSM-73 | Mouse C3H/He | 1 week+ |

TABLE 3

| Abdominal Dropsy Name of Tumor | Name of Host-Animal | Freezing Time (year) | Biocell Number (%) Freezing | Biocell Number (%) Thawing | Viable Cell Count (%) |
|---|---|---|---|---|---|
| M-1498 | Mouse C57BL | 0.5 | 99 | 95 | 96 |
| MM-102 | Mouse C3H/He | 1.5 | 90 | 83 | 92 |
|  |  | 2.5 |  | 72 | 80 |
| FM3A | Mouse C3H/He | 5.0 | 97 | 93 | 96 |
|  |  | 2.0 | 94 | 90 | 96 |
| S-37 | Mouse JCR/JCL | 3.0 | 91 | 71 | 78 |
|  |  | 5.0 | 88 | 79 | 90 |
| Yoshida-Sarcoma | Rat Donryu | 3.0 | 91 | 31 | 34 |
|  |  | 4.0 |  | 54 | 59 |

As can be understood from the above description, according to the present invention, the slow freezing of an animal cell can be effected at a desired cooling speed by using a cryopreservation container of the present invention which can be received in an existing deep freezer which has been widely used in laboratories or works. It should be particularly appreciated that the slow freezing of an animal cell can be performed without using a mechanical or electrical control means in the present invention.

I claim:

1. A cryopreservation container comprising a bottomed hollow container body, said container body including an inner wall portion having an open top forming a hollow container portion, an outer wall portion surrounding said inner wall portion, and a hollow heat conductivity-retarded liquid portion between said inner wall portion and said outer wall portion, a lid for closing said hollow container portion, and heat conductivity-retarded liquid enclosed within said hollow heat conductivity-retarded liquid portion of said container body, and wherein said heat conductivity-retarded liquid comprises a liquid which provides, when ambient temperature of the cryopreservation container is $-60°$ C. $\sim -100°$ C., a cooling rate in said container body of $-0.5°$ C./min. $\sim -2°$ C./min.

2. The cryopreservation container according to claim 1, wherein said container body, said inner wall portion and said outer wall portion are cylindrically shaped.

3. The cryopreservation container according to claim 2, including a ring member connecting an upper portion of each of said inner wall portion and said outer wall portion to each other.

4. The cryopreservation container according to claim 3, wherein said ring member includes at least one aperture.

5. The cryopreservation container according to claim 4, wherein said at least one aperture is sealed.

6. The cryopreservation container according to claim 1, wherein said lid is removably attached to said container body.

7. The cryopreservation container according to claim 1, wherein said lid comprises a heat insulative solid material.

8. The cryopreservation container according to claim 1, wherein said lid comprises a hollow portion in which heat conductivity-retarded liquid is enclosed.

9. The cryopreservation container according to claim 1, wherein said heat conductivity-retarded liquid comprises a solution of acetone in water.

10. The cryopreservation container according to claim 9, wherein said solution of acetone in water comprises 20~40 volume % of acetone in water.

11. The cryopreservation container according to claim 1, wherein said heat conductivity-retarded liquid comprises ethanol.

12. The cryopreservation container according to claim 1, wherein said container body is composed of a synthetic resin.

13. The cryopreservation container according to claim 12, wherein said synthetic resin comprises polyethylene.

14. A combination of a cryopreservation container and an enclosure container in which an animal cell to be frozen and preserved is enclosed together with a cryopreservation medium, said combination comprising:
a cryopreservation container comprising a bottomed hollow container body, said container body including an inner wall portion having an open top forming a hollow container portion, an outer wall portion surrounding said inner wall portion, and a hollow heat conductivity-retarded liquid portion between said inner wall portion and said outer wall portion, a lid for closing said hollow container portion, and heat conductivity-retarded liquid enclosed within said hollow heat conductivity-retarded liquid portion of said container body, wherein said heat conductivity-retarded liquid comprises a liquid which provides, when ambient temperature of the cryopreservation container is $-60°$ C. $\sim -100°$ C., a cooling rate in said container body of $-0.5°$ C./min. $\sim -2°$ C./min; and
an enclosure container for enclosing an animal cell to be frozen and preserved together with a cryopreservation medium.

15. The combination of a cryopreservation container and an enclosure container according to claim 14, wherein said enclosure container is housed in said hollow container portion of said container body.

16. The combination of a cryopreservation container and an enclosure container according to claim 14, wherein said enclosure container comprises a metal tube.

17. The combination of a cryopreservation container and an enclosure container according to claim 16, wherein said metal tube is composed of aluminum.

18. The combination of a cryopreservation container and an enclosure container according to claim 16, wherein said enclosure container is composed of aluminum alloy.

19. The combination of a cryopreservation container and an enclosure container according to claim 14, further including a cryopreservation medium within said enclosure container.

* * * * *